United States Patent
Zhang

(10) Patent No.: US 7,913,553 B2
(45) Date of Patent: Mar. 29, 2011

(54) CONNECTION STRENGTH TESTING DEVICE

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 187 days.

(21) Appl. No.: 12/331,439

(22) Filed: Dec. 10, 2008

(65) Prior Publication Data

US 2010/0024564 A1 Feb. 4, 2010

(30) Foreign Application Priority Data

Jul. 31, 2008 (CN) .......................... 2008 1 0303256

(51) Int. Cl.
*G01B 21/08* (2006.01)
(52) U.S. Cl. ....................... 73/150 A; 73/827
(58) Field of Classification Search ................. 73/150 A, 73/827–830
See application file for complete search history.

(56) References Cited

U.S. PATENT DOCUMENTS

| | | | | |
|---|---|---|---|---|
| 4,448,568 A * | 5/1984 | Gentry et al. | ............... | 405/168.3 |
| 5,404,751 A * | 4/1995 | Beran et al. | .................. | 73/150 A |
| 5,487,308 A * | 1/1996 | Demarest et al. | ................ | 73/827 |
| 5,918,284 A * | 6/1999 | Blanch et al. | .................... | 73/827 |
| 6,662,666 B2 * | 12/2003 | Hasegawa | ........................ | 73/831 |
| 7,035,715 B1 * | 4/2006 | Burkhead | ...................... | 700/239 |
| 7,451,666 B2 * | 11/2008 | Johanson | ........................ | 73/866 |
| 7,757,996 B2 * | 7/2010 | Jacobs | ............................. | 248/64 |

\* cited by examiner

*Primary Examiner* — Max Noori
(74) *Attorney, Agent, or Firm* — Zhigang Ma

(57) ABSTRACT

A strength testing device for testing a connection strength between two articles when a connection interface therebetween located vertically and includes a blade member, a suspending member, and a handle. The suspending member includes a relay portion, a first connection portion and a second portion disposed at two opposite ends of the relay portion. The blade member includes a blade seating on one of the articles. A holder is formed on the second connection portion to hold a critical weight to break the two articles along the connection interface. A gravity line of the weight crosses with the blade.

11 Claims, 3 Drawing Sheets

CONNECTION STRENGTH TESTING DEVICE

BACKGROUND

1. Technical Field

The present disclosure relates to testing devices and, particularly, to a connection strength testing device.

2. Description of Related Art

In manufacturing, two articles are often connected by adhesives or soldering, for instance, rubber pads are adhesively attached to a base of a notebook computer to providing support therefor. Strength of the connection between the pads and the base may then be tested by use of a thrust meter. An operator forces the thrust meter to exert a predetermined force on the connection interface between one of the pads and the base for a certain time. However, it is not only that the testing procedure is inconvenient, but also that it is hard to get a stable and accurate connection strength value because of vibration or movement during the test.

What is needed, therefore, is to provide a connection strength testing device to overcome the above described shortcomings.

DETAILED DESCRIPTION

Figure 1:
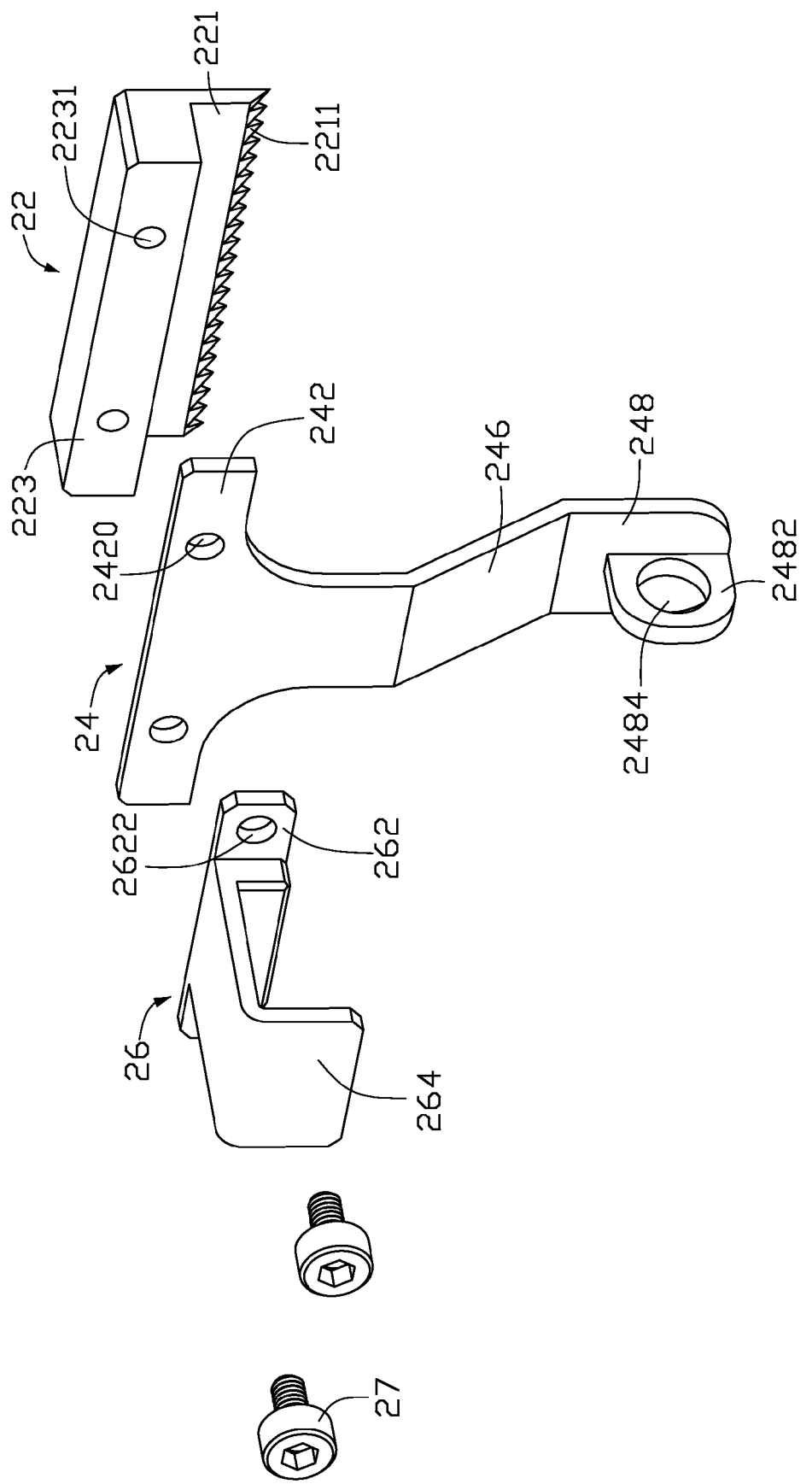
FIG. 1 is an exploded, isometric view of an embodiment of a connection strength testing device.
Figure 3:
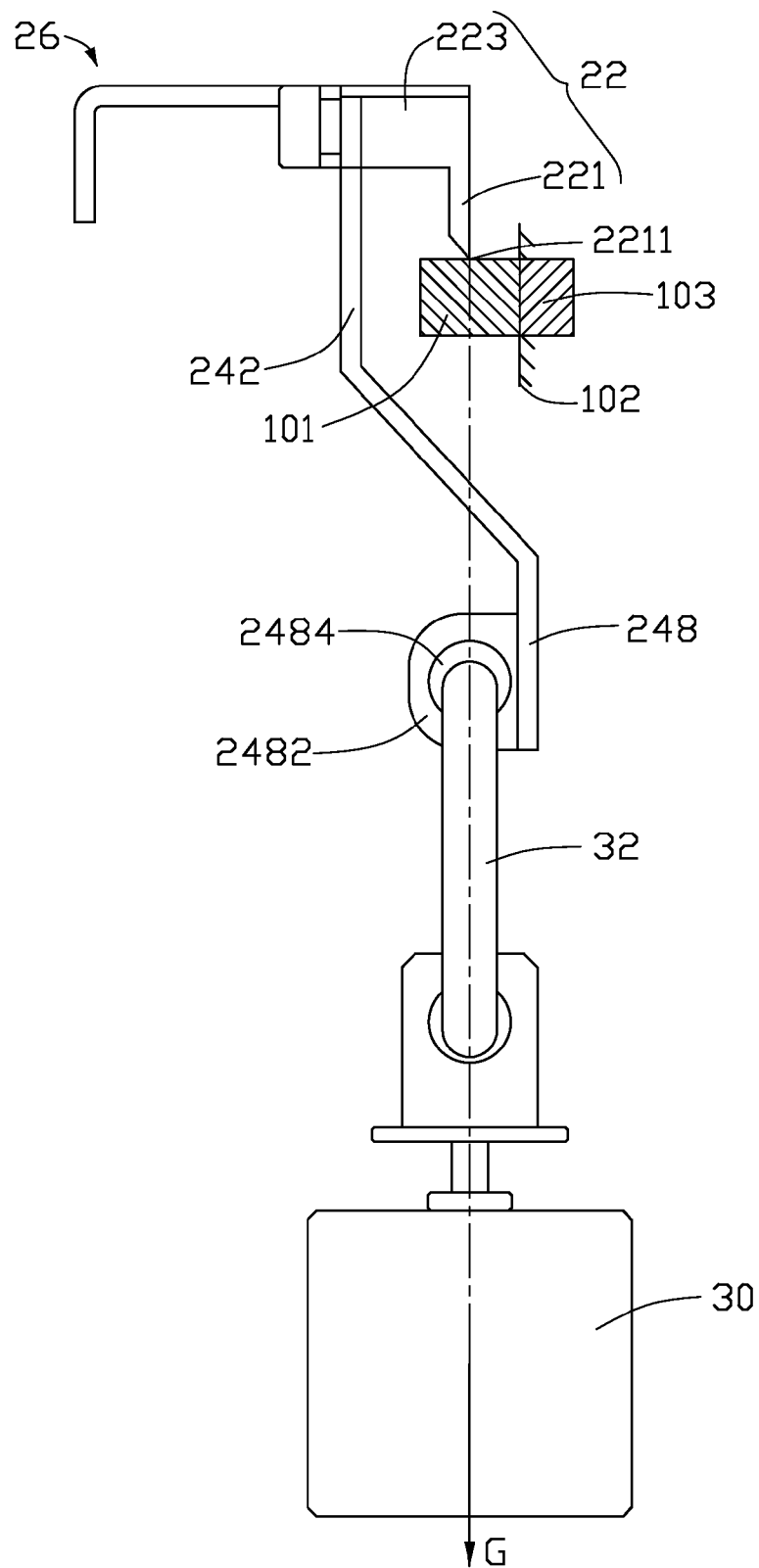
FIG. 3 is a side plan view of FIG. 2 together with a weight.

Referring to FIGS. 1 and 3, an embodiment of a strength testing device for testing a connection strength between two articles 101, 102 is presented. The test device includes a blade member 22, a suspending member 24, and a handle 26.

The blade member 22 includes a blade 221, and a protruding portion 223 extending perpendicularly from the blade 221. A plurality of teeth 2211 is formed at a distal edge of the blade 221. A pair of fixing holes 2231 is defined in the protruding portion 223.

The suspending member 24 includes a relay portion 246, a first connecting portion 242, and a second connecting portion 248. In this embodiment, the relay portion 246, the first connecting portion 242, and the second connecting portion 248 are plates. The first connecting portion 242 and the second connecting portion 248 are slantingly disposed at two opposite ends of the relay portion 246, extending oppositely on parallel planes. The first connecting portion 242 is generally T-shaped and includes a pair of through holes 2420 defined in a wide part thereof, corresponding to the fixing holes 2231 of the blade member 22. A holder 2482 is formed at one side of the second connecting portion 248, located between the second connecting portion 248 and an inverse extension plane of the first connecting portion 242. In this embodiment, the holder 2482 is a tab perpendicularly extending from the second connecting portion 248 and a through hole 2484 is defined in the tab for holding a critical weight 30 via a hook, to apply a force on one of the articles to break the two articles 101, 103 along the connection interface 102.

The handle 26 is generally L-shaped and includes a fixing board 262 formed at one end thereof and a L-shaped handling portion 264. A pair of apertures 2622 is defined in the fixing board 262.

Figure 2:
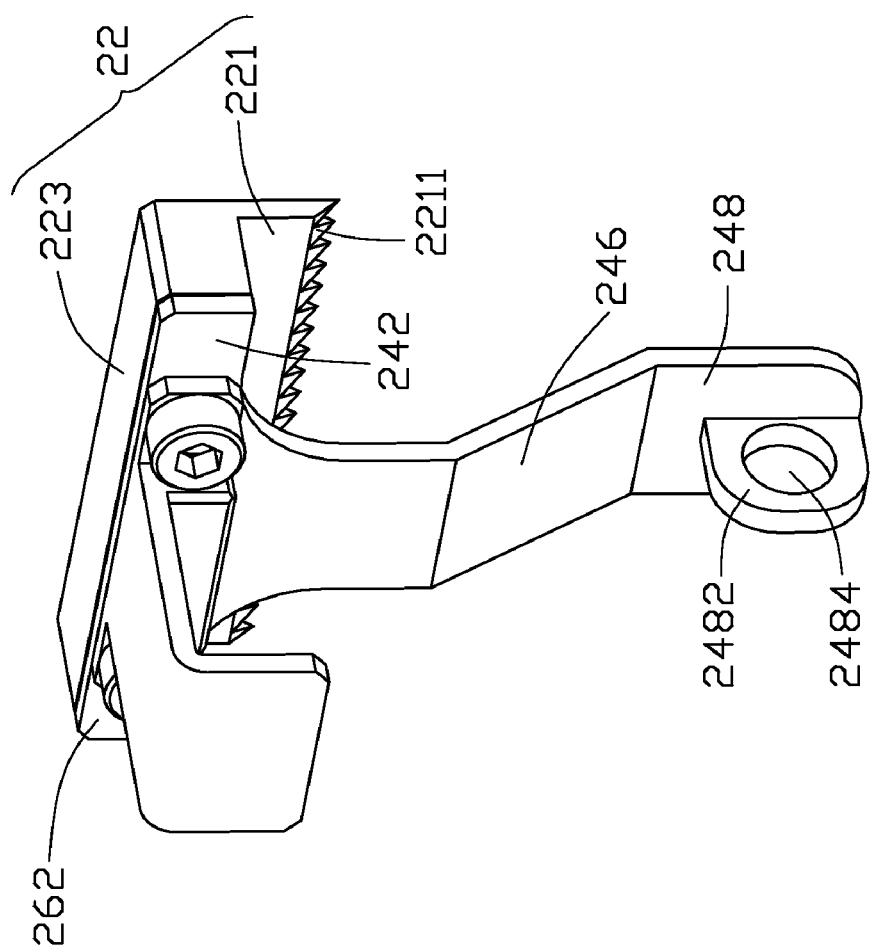
FIG. 2 is an assembled, isometric view of the testing device of FIG. 1.

Referring to FIG. 2, in assembly, the handle 26, the suspending member 24, and the blade member 22 are assembled, with a pair of fasteners 27 extending through the apertures 2622 of the handle 26, then the through holes 2420 of the suspending member 24 to engage in the fixing holes 2231 of the blade member 22. The blade member 22 is located at a first side of the suspending member 24 and the holder 2482 is located at a second side of the suspending member 24 opposite to the first side.

Referring to FIG. 3, in use, the connecting interface 102 between the two articles 101, 103 is vertically located. The blade 221 of the blade member 22 is vertically seated on the article 101 or 103. A gravity line of the weight 30 crosses at the blade 221. In this embodiment, the gravity line of the weight 30 aligns with the blade 221. Thus, the weight 30 can directly test the connection strength between two articles 101, 103.

It is to be understood, however, that even though numerous characteristics and advantages of the embodiments have been set forth in the foregoing description, together with details of the structure and function of the embodiments, the disclosure is illustrative only, and changes may be made in details, especially in matters of shape, size, and arrangement of parts within the principles of the embodiments to the full extent indicated by the broad general meaning of the terms in which the appended claims are expressed.

What is claimed is:

1. A strength testing device testing a connection strength between two articles bonded together with a connection interface vertically positioned in during test, the strength testing device comprising:

a blade member comprising a blade and a protruding portion perpendicularly extending from the blade, the blade seating on a top of one of the articles; and a suspending member comprising a relay portion, and a first and a second connecting portions extending from opposite ends of the relay portion, wherein the first connecting portion is fixed to a free end of the protruding portion away from the blade to prevent the suspending member from engaging with said one of the two articles, a holder is formed on the second connection portion to hold a critical weight to apply a downward vertical force on said one of the two articles to break the two articles along the connection interface, a gravity line of the weight crosses at the blade.

2. The strength testing device of claim 1, wherein the first connecting portion and the second connecting portion are slantingly disposed at two opposite ends of the relay portion, extending oppositely and one paralleling to the other.

3. The strength testing device of claim 1, wherein the blade member is attached to the first connecting portion at a first side of the suspending member, the holder is attached to the second connecting portion at a second side of the suspending member opposite to the first side.

4. The strength testing device of claim 1, wherein the blade comprises a plurality of teeth formed thereon to seat the blade on one of the articles.

5. The strength testing device of claim 1, wherein a pair of fixing holes is defined in the protruding portion, the first connecting portion is generally T-shaped, a pair of through holes is defined in a wide part of the first connecting portion, a pair of fasteners extends through the through holes to engage in the fixing holes, for attaching the blade member to the suspending member.

6. The strength testing device of claim 1, further comprising a handle, wherein the blade comprises a protruding portion perpendicular to the blade, a pair of fixing holes is defined in the protruding portion, the first connecting portion is generally T-shaped, a pair of through holes is defined in a wide part of the first connecting portion, a connecting board extends from one end of the handle and defines a pair of apertures therein, a pair of fasteners sequentially extends through the apertures and the through holes to engage in the fixing holes, for assembling the handle, the suspending member, and the blade member together.

7. The strength testing device of claim 1, wherein the a gravity line of the weight is substantially in alignment with the blade.

8. A strength testing method for testing a connection strength between two articles, comprising:
 positioning a connecting interface between the two articles vertically;
 providing a blade member comprising a blade seated on a top of one of the articles;
 providing a suspending member extending downwards without engaging with the blade member, and comprising a first connecting portion fixed to a blade member, and a second connecting portion disposed below said one of the articles;
 providing a critical weight attached to the second connecting portion to make the gravity line of the weight crossing at the blade, thereby causing a downward vertical force applied to said one of the articles to break the two articles along the connection interface.

9. The strength testing method of claim 8, wherein the suspending member further comprises a relay portion, the first connecting portion and the second connecting portion are slantingly disposed at two opposite ends of the relay portion, extending oppositely and one paralleling to the other.

10. The strength measure method of claim 9, wherein the blade member is attached to the first connecting portion at a first side of the suspending member, the holder is attached to the second connecting portion at a second side of the suspending member opposite to the first side.

11. The strength measure method of claim 8, wherein the blade comprises a plurality of teeth formed thereon to seat the blade on one of the articles.

* * * * *